United States Patent
Ferguson

(10) Patent No.: US 6,861,546 B1
(45) Date of Patent: Mar. 1, 2005

(54) METHOD OF PURIFYING ALKOXYSILANES

(75) Inventor: Stephen Paul Ferguson, Midland, MI (US)

(73) Assignee: Dow Corning Corporation, Midland, MI (US)

(*) Notice: Subject to any disclaimer, the term of this patent is extended or adjusted under 35 U.S.C. 154(b) by 0 days.

(21) Appl. No.: 10/770,999

(22) Filed: Feb. 3, 2004

(51) Int. Cl.⁷ .................................................. C07F 7/10
(52) U.S. Cl. ........................ 556/413; 556/438; 556/429; 556/460; 549/541
(58) Field of Search ................................. 556/438, 429, 556/413, 460, 470, 466; 549/541

(56) References Cited

U.S. PATENT DOCUMENTS

| | | | |
|---|---|---|---|
| 3,792,071 A | 2/1974 | Nitzsche et al. | ......... 260/448.8 |
| 5,374,761 A | 12/1994 | Bank | ........................... 556/471 |
| 6,255,514 B1 | 7/2001 | Brand et al. | ................. 556/470 |

OTHER PUBLICATIONS

Kirk Othmer Encyclopedia of Chemical Technology, Fourth Edition (1993), vol. 10, pp. 125–180.

*Primary Examiner*—Samuel Barts
(74) *Attorney, Agent, or Firm*—Jim L. De Cesare

(57) ABSTRACT

A mixture containing a monohydric alkyl alcohol and an alkoxysilane is purified by (i) adding an organic salt or an inorganic salt to the monohydric alkyl alcohol and the alkoxysilane; (ii) mixing the organic or inorganic salt with the monohydric alkyl alcohol and the alkoxysilane; and (iii) separating from (ii) a first phase containing the alkoxysilane, and a second phase containing the monohydric alcohol and the organic or inorganic salt. The preferred salt is lithium chloride, and the monohydric alkyl alcohol is most typically methyl alcohol or ethyl alcohol.

7 Claims, No Drawings

US 6,861,546 B1

METHOD OF PURIFYING ALKOXYSILANES

CROSS REFERENCE TO RELATED APPLICATIONS

Not applicable.

FIELD OF THE INVENTION

This invention is related to a method for purifying alkoxysilanes other than trimethoxysilane $HSi(OCH_3)_3$. In particular, the method involves the removal of monohydric alkyl alcohols from mixtures containing monohydric alkyl alcohols and alkoxysilanes.

BACKGROUND OF THE INVENTION

U.S. Pat. No. 6,255,514 (Jul. 3, 2001), hereafter referred to as the '514 patent, is directed to the isolation of trimethoxysilane from a trimethoxysilane/methanol mixture. The '514 patent is limited strictly to trimethoxysilane, and no other alkoxysilane is mentioned in the entirety of the text of the '514 patent. However, the present method is directed to the isolation and/or purification of alkoxysilanes other than trimethoxysilane, from alkoxysilane/monohydric alkyl alcohol mixtures.

SUMMARY OF THE INVENTION

The invention is directed to a method of purifying a mixture containing a monohydric alkyl alcohol and an alkoxysilane. The alkoxysilane is a compound having the formula $R_mSi(OR')_{4-m}$ where R is hydrogen, a $C_1$ to $C_8$ monovalent hydrocarbon group, or a functional group; R' is a $C_1$ to $C_8$ monovalent hydrocarbon group; m is zero, 1, 2, or 3; except that R is not hydrogen when R' is methyl and m is one.

The method is carried out by:
(i) adding an organic salt or an inorganic salt to the monohydric alkyl alcohol and the alkoxysilane;
(ii) mixing the organic or inorganic salt with the monohydric alkyl alcohol and alkoxysilane; and
(iii) separating from (ii) a first phase containing the alkoxysilane, and a second phase containing the monohydric alcohol and the organic or inorganic salt.

The preferred salt is lithium chloride, and the monohydric alkyl alcohol is most typically methyl alcohol or ethyl alcohol. These and other features of the invention will become apparent from a consideration of the detailed description.

BRIEF DESCRIPTION OF THE DRAWING

Not applicable.

DETAILED DESCRIPTION OF THE INVENTION

Alkoxysilanes are often produced in commercial quantities by liquid or vapor-phase reactions of chlorosilanes with alcohols, e.g., U.S. Pat. No. 3,792,071 (Feb. 12, 1974), and U.S. Pat. No. 5,374,761 (Dec. 20, 1961). However, the purification and separation of the products of this reaction are often complicated by the formation of an azeotrope of the alkoxysilane with the alcohol. This requires the use of complex distillation techniques to separate the alcohol from the alkoxysilane. According to the present invention, however, purification and separation are simplified, and the alcohol is simply salted out of the reaction product and into a liquid phase by the addition of an organic or inorganic salt. The purified alkoxysilane can then be recovered as a liquid phase separate from the liquid phase containing the alcohol and the salt.

As is well known by skilled workers in the art, salting out is a technique whereby liquids can be made immiscible, so that they can be separated one from the other, i.e., when salts such as potassium carbonate are added to a solution of methanol in water, two liquid phases are produced.

Alkoxysilanes within the scope of the present invention include compounds having the formula $R_mSi(OR')_{4-m}$ wherein R is hydrogen, a $C_1$ to $C_8$ monovalent hydrocarbon group, or a functional group; R' is a $C_1$ to $C_8$ monovalent hydrocarbon group; m is zero, 1, 2, or 3; except that R is not hydrogen when R' is methyl and m is one. As defined, and as used herein, the term alkoxysilane means alkoxysilanes other than trimethoxysilane $HSi(OCF_3)_3$.

Some examples of suitable hydrocarbon groups include alkyl groups such as methyl, ethyl, propyl and octyl; aryl groups such as phenyl, tolyl, and xylyl; and aralkyl groups such as benzyl. Some examples of functional groups are acryloxy, methacryloxy, mercapto, epoxy, chloroalkyl, vinyl, allyl, amino, and diamino.

Alkoxysilanes most preferred according to the invention include benzyltriethoxysilane $C_6H_5CH_2Si(OC_2H_5)_3$, n-butyltrimethoxysilane $CH_3CH_2CH_2CH_2Si(OCH_3)_3$, dimethyldimethoxysilane $(CH_3)_2Si(OCH_3)_2$, dimethyldiethoxysilane $(CH_3)_2Si(OC_2H_5)_2$, diethyldiethoxysilane $(C_2H_5)_2Si(OC_2H_5)_2$, dimethylethoxysilane $(CH_3)_2HSi(OC_2H_5)$, diphenyldimethoxysilane $(C_6H_5)_2Si(OCH_3)_2$, ethyltrimethoxysilane $C_2H_5Si(OCH_3)_3$, ethyltriethoxysilane $C_2H_5Si(OC_2H_5)_3$, hexyltrimethoxysilane $CH_3(CH_2)_4CH_2Si(OCH_3)_3$, methyldimethoxysilane $CH_3HSi(OCH_3)_2$, methyldiethoxysilane $CH_3HSi(OC_2H_5)_2$, methyltrimethoxysilane $CH_3Si(OCH_3)_3$, methyltriethoxysilane $CH_3Si(OC_2H_5)_3$, octyltrimethoxysilane $CH_3(CH_2)_6CH_2Si(OCH_3)_3$, phenyltrimethoxysilane $(C_6H_5)Si(OCH_3)_3$, n-propyltrimethoxysilane $CH_3CH_2CH_2Si(OCH_3)_3$, p-tolyltrimethoxysilane $CH_3(C_6H_4)Si(OCH_3)_3$, trimethylethoxysilane $(CH_3)_3Si(OC_2H_5)$, cyclohexylmethyldimethoxysilane $(C_6H_{11})CH_3Si(OCH_3)_2$, and dicyclopentyldimethoxysilane $(C_5H_9)_2Si(OCH_3)_2$.

Some examples of alkoxysilanes containing functional groups according to the invention include aminoethylaminopropyltrimethoxysilane $NH_2(CH_2)_2NH(CH_2)_3Si(OCH_3)_3$, 3-aminopropyltriethoxysilane $NH_2(CH_2)_3Si(OC_2H_5)_3$, vinyltrimethoxysilane $H_2C=CHSi(OCH_3)_3$, vinyltriethoxysilane $H_2C=CHSi(OC_2H_5)_3$, 3-glycidoxypropyltrimethoxysilane $H_2C(O)CHCH_2O(CH_2)_3Si(OCH_3)_3$, 3-acryloxypropyltrimethoxysilane $H_2C=CHC(O)O(CH_2)_3Si(OCH_3)_3$, 3-acryloxypropyldimethylmethoxysilane $H_2C=CHC(O)O(CH_2)_3Si(CH_3)_2(OCH_3)$, 3-acryloxypropylmethyldimethoxysilane $H_2C=CHC(O)O(CH_2)_3Si(CH_3)(OCH_3)_2$, 3-methacryloxypropyldimethylethoxysilane $H_2C=C(CH_3)C(O)O(CH_2)_3Si(CH_3)_2(OC_2H_5)$, 3-methacryloxypropyldimethylmethoxysilane $H_2C=C(CH_3)C(O)O(CH_2)_3Si(CH3)_2(OCH_3)$, 3-methacryloxypropylmethyldiethoxysilane $H_2C=C(CH_3)C(O)O(CH_2)_3Si(CH_3)(OC_2H_5)_2$, 3-methacryloxypropylmethyldimethoxysilane $H_2C=C(CH_3)C(O)O(CH_2)_3Si(CH_3)(OCH_3)_2$, 3-methacryloxymethyltriethoxysilane $H_2C=C(CH_3)C(O)O(CH_2)Si(OC_2H_5)_3$, 3-methacryloxymethyltrimethoxysilane $H_2C=C(CH_3)C(O)O(CH_2)Si(OCH_3)_3$, 3-methacryloxypropyltriethoxysilane $H_2C=C(CH_3)C(O)O(CH_2)_3Si(OC_2H_5)_3$, 3-methacryloxypropyltrimethoxysilane $H_2C=C(CH_3)C(O)O(CH_2)_3Si(OCH_3)_3$, 3-mercaptopropyltrimethoxysilane $HS(CH_2)_3Si(OCH_3)_3$, and 3-chloropropyltrimethoxysilane $Cl(CH_2)_3Si(OCH_3)_3$.

While the present method is especially useful for separating alkoxysilanes from methyl alcohol and ethyl alcohol, it is applicable to the separation of alkoxysilanes from other monohydric alkyl alcohols such as propyl alcohol, isopropyl alcohol, isobutyl alcohol, n-pentyl alcohol, and n-hexyl alcohol, for example.

The method according to the invention encompasses the use of either an organic salt or an inorganic salt. Some examples of suitable inorganic salts that can be used include halides, perchlorates, tetrafluoroborates, sulfates and nitrates. Some compounds most preferred are sodium chloride, lithium chloride, calcium chloride, ferrous chloride, and zinc chloride. Some examples of suitable organic salts that can be used include acetates and carboxylates such as sodium acetate, ferric acetate, ferrous acetate, zinc acetate, potassium acetate, sodium salicylate, potassium salicylate, and potassium ethylhexoate. The most preferred of the salts is lithium chloride.

If desired, a solvent can be used to facilitate the phase separation necessary to achieve purification. Most preferred are nonpolar solvents including unbranched higher alkanes such as dodecane, tridecane, tetradecane, and/or mixtures thereof. Some other suitable nonpolar solvents that can be used include (i) diphenylalkanes such as diphenylmethane, 1,2-diphenylethane, and 1,6-diphenylhexane; (ii) dialkylbenzenes such as dimethylbenzene, diethylbenzene, and di-t-butylbenzene; (iii) linear alkylbenzenes such as toluene, ethylbenzene, butylbenzene, and octylbenzene; and (iv) fluorinated hydrocarbons such as hexafluorobenzene. During the process of salting out the monohydric alkyl alcohol, the nonpolar solvent and the alkoxysilane form an upper phase, while the organic or inorganic salt and the monohydric alkyl alcohol form an upper phase.

The amount of alkoxysilane and monohydric alkyl alcohol is generally in a range of about 80–99 percent by weight of alkoxysilane and 1–20 percent by weight of monohydric alkyl alcohol. The amount of the organic or inorganic salt used in the method should be at least about 0.5 percent by weight, based on the weight of the alkoxysilane and monohydric alkyl alcohol. Preferably, the amount of the organic or inorganic salt is about 0.5 to less than about 10 percent by weight, based on the weight of the alkoxysilane and monohydric alkyl alcohol. When a solvent is used, it can be present in varying amounts depending upon the particulars of the extraction being carried out, but generally it comprises an amount of about the same as the amount of the monohydric alcohol being used, to as much as about twice the amount of monohydric alcohol.

The method can be carried out at any convenient temperature, generally temperatures within the range of −20° C. to about 65° C., and at any convenient pressure, most typically atmospheric pressure. The method can be carried out in a variety of apparatus or devices known to be useful for conducting liquid—liquid extractions. Some examples of suitable devices that can be used include un-agitated columns such as spray columns, packed columns, and perforated plate columns. Pulsed columns that can be used include pulse-packed columns, pulse sieve-plate columns, controlled cycling columns, and pulsed mixer-settlers.

Rotary devices that can be used include rotary agitation contractors such as mixer-settlers, rotating disk contractors, and asymmetric rotating disk extractors. Reciprocating devices that can be used include reciprocating plate columns such as perforated-plate columns, sieve-plate columns with downcomer, and vaned-perforation plate columns. Centrifugal extractors that can be used include Podbielniak extractors, Delaval extractors, Luwesta extractors, and Robatel extractors. Miscellaneous devices that can be used include static mixers, vibrating plate extractors, ultrasonic extractors, and parametric pumping extractors.

The arrangement of the flow stream of the different phases in these devices can be cocurrent, crosscurrent or countercurrent, and it can be conducted with or without recirculation of the phase rich in the alkoxysilane. The details of these and other kinds of apparatus and devices useful in Liquid—Liquid Extraction are set forth in the Kirk Othmer *Encyclopedia of Chemical Technology*, Fourth Edition (1993), Volume 10, Pages 125–180.

EXAMPLES

The following examples are set forth in order to illustrate the invention in more detail. Unless otherwise specified, all weights in the Tables are percent by weight.

Example 1

Methyldimethoxysilane

A mixture of 48.14 gram of methyldimethoxysilane and 0.27 gram of lithium chloride were mixed for one hour. The composition contained 80 percent methyldimethoxysilane, 4.7 percent methanol, and the balance was primarily methyltrimethoxysilane, as determined by gas chromatography. All of the lithium chloride dissolved into solution. The mixture was then allowed to stand and two phases formed. The two phases were analyzed by gas chromatography, and the results of the analysis are shown in Table 1.

TABLE 1

Example 1

| | | Liquid Composition by Gas Chromatography | | |
|---|---|---|---|---|
| Solution Description | Weight (gram) | Methanol (Percent) | Methyldi-methoxysilane (Percent) | Methyltri-methoxysilane (Percent) |
| Feed Solution | 48.1 | 4.7 | 80.1 | 13.1 |
| Upper Phase | 46.4 | 2.8 | 81.4 | 13.4 |
| Lower Phase | 1.18 | 88.3 | 8.4 | 2.2 |

Example 2

Methyldiethoxysilane

Lithium chloride (10.6 gram) was added to a solution of 5.4 percent ethanol and 86.5 percent methyldiethoxysilane (572.6 gram). Upon mixing, all of the lithium chloride dissolved. Two phases formed after the mixing was stopped. The top phase weighed 527.4 gram and the bottom phase weighed 46.3 gram.

Example 3

Dimethyldimethoxysilane 6.1 gram of lithium chloride was added to a solution of dimethyldimethoxysilane and methanol. Upon mixing, essentially all of the lithium chloride dissolved. Two phases formed after the mixing was stopped. The top phase was analyzed by gas chromatography, and the results of the analysis are shown in Table 2.

TABLE 2

Example 3

| Solution Description | Weight (gram) | Liquid Composition | |
|---|---|---|---|
| | | Methanol (Percent) | Dimethyldimethoxysilane (Percent) |
| Feed Solution | 572.6 | 12.1 | 86.6 |
| Upper Phase | 527.4 | 8.6 | 89.8 |
| Lower Phase | 46.3 | Not measured | Not measured |

Example 4

Methyltrimethoxysilane 20.3 gram of lithium chloride was added to a solution of methyltrimethoxysilane and methanol. Upon mixing, essentially all of the lithium chloride dissolved. Two phases formed after the mixing was stopped. The top phase was analyzed by gas chromatography, and the results of the analysis are shown in Table 3.

TABLE 3

Example 4

| Solution Description | Weight (gram) | Liquid Composition | |
|---|---|---|---|
| | | Methanol (Percent) | Methyltrimethoxysilane (Percent) |
| Feed Solution | 600.7 | 13.9 | 85.6 |
| Upper Phase | 503.0 | 3.1 | 96.3 |
| Lower Phase | 95.2 | Not measured | Not measured |

Example 5

3-Methacryloxypropyltrimethoxysilane 5.98 gram of lithium chloride were added to a solution of 3-methacryloxypropyltrimethoxysilane and methanol. All of the lithium chloride dissolved after mixing. When the solution was allowed to settle, two phases formed. It was noted that the top phase was rich in methanol rather than being rich in the alkoxysilane. This is a unique feature of the invention, as compared to other alkoxysilanes, where the alcohol phase is the heavy phase. The composition of each phase was determined using gas chromatography, and the results of the analysis are shown in Table 4.

TABLE 4

Example 5

| Solution Description | Weight (gram) | Liquid Composition | |
|---|---|---|---|
| | | Methanol (Percent) | 3-methacryloxypropyl-trimethoxysilane (Percent) |
| Feed Solution | 515.1 | 2.17 | 88.4 |
| Upper Phase | 10.8 | 82.1 | 15.0 |
| Lower Phase | 502.3 | 1.21 | 90.5 |

As noted above, this example represents a unique feature of the present invention, in that contrary to the teaching in the '514 patent, the alkoxysilane resides in the lower phase, and the monohydric alcohol and the organic or inorganic salt are in the upper phase. According to the teaching of the '514 patent, the alkoxysilane resides in the upper phase, and the monohydric alcohol and the organic or inorganic salt are in the lower phase.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A method of purifying a mixture containing a monohydric alkyl alcohol and an alkoxysilane having the formula $R_mSi(OR')_{4-m}$ where R is a functional group; R' is a $C_1$ to $C_8$ monovalent hydrocarbon group; m is zero, 1, 2, or 3; except that R is not hydrogen when R' is methyl and m is one; the method comprising:

(i) adding an organic salt or an inorganic salt to the monohydric alkyl alcohol and the alkoxysilane;

(ii) mixing the organic or inorganic salt with the monohydric alkyl alcohol and alkoxysilane; and (iii) separating from (ii) a first phase containing the alkoxysilane, and a second phase containing the monohydric alcohol and the organic or inorganic salt; provided the first phase containing the alkoxysilane is the lower phase, and the second phase containing the monohydric alcohol and the organic or inorganic salt is the upper phase.

2. A method according to claim 1 in which the functional group is selected from the group consisting of acryloxy, methacryloxy, mercapto, epoxy, chloroalkyl, vinyl, allyl, amino, and diamino.

3. A method according to claim 2 in which the alkoxysilane is a compound selected from the group consisting of aminoethylaminopropyltrimethoxysilane, 3-aminopropyltriethoxysilane, 3-glycidoxypropyltrimethoxysilane, 3-acryloxypropyltrimethoxysilane, 3-acryloxypropyldimethylmethoxysilane, 3-acryloxypropylmethyldimethoxysilane, 3-methacryloxymethyltriethoxysilane, 3-methacryloxymethyltrimethoxysilane, 3-methacryloxypropyldimethylethoxysilane, 3-methacryloxypropyldimethylmethoxysilane, 3-methacryloxypropylmethyldiethoxysilane, 3-methacryloxypropylmethyldimethoxysilane, 3-methacryloxypropyltriethoxysilane, 3-methacryloxypropyltrimethoxysilane, and 3-mercaptopropyltrimethoxysilane.

4. A method according to claim 1 in which the salt is lithium chloride.

5. A method according to claim 1 in which the monohydric alkyl alcohol is methyl alcohol or ethyl alcohol.

6. A method according to claim 1 in which the functional group is acryloxy or methacryloxy.

7. A method according to claim 6 in which the lower first phase contains 3-methacryloxypropyltrimethoxylsilane.

* * * * *